United States Patent
Park et al.

(10) Patent No.: US 10,888,621 B2
(45) Date of Patent: Jan. 12, 2021

(54) INJECTABLE TISSUE ADHESIVE HYDROGEL INCLUDING GAMMA-CYCLODEXTRIN AND BIOMEDICAL USE THEREOF

(71) Applicants: AJOU UNIVERSITY INDUSTRY—ACADEMIC COOPERATION FOUNDATION, Suwon-si (KR); INCHEON UNIVERSITY INDUSTRY ACADEMIC COOPERATION FOUNDATION, Incheon (KR)

(72) Inventors: Ki Dong Park, Seoul (KR); Kyung Min Park, Anyang-si (KR); Yun Ki Lee, Seongnam-si (KR); Thi Thai Thanh Hoang, Suwon-si (KR); Thi Phuong Le, Suwon-si (KR)

(73) Assignees: AJOU UNIVERSITY INDUSTRY—ACADEMIC COOPERATION FOUNDATION, Suwon-si (KR); INCHEON UNIVERSITY INDUSTRY ACADEMIC COOPERATION FOUNDATION, Incheon (KR)

( * ) Notice: Subject to any disclaimer, the term of this patent is extended or adjusted under 35 U.S.C. 154(b) by 112 days.

(21) Appl. No.: 15/475,948

(22) Filed: Mar. 31, 2017

(65) Prior Publication Data
US 2017/0281781 A1 Oct. 5, 2017

(30) Foreign Application Priority Data

Apr. 1, 2016 (KR) .................. 10-2016-0040153

(51) Int. Cl.
| | | |
|---|---|---|
| *A61K 38/21* | (2006.01) | |
| *A61K 47/40* | (2006.01) | |
| *A61K 9/00* | (2006.01) | |
| *A61K 9/06* | (2006.01) | |
| *A61L 26/00* | (2006.01) | |

(52) U.S. Cl.
CPC ............ *A61K 47/40* (2013.01); *A61K 9/0019* (2013.01); *A61K 9/0024* (2013.01); *A61K 9/06* (2013.01); *A61L 26/008* (2013.01); *A61L 26/0066* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 2012/0100103 A1* | 4/2012 | Park | ................. | A61L 27/52 424/85.2 |
| 2015/0374838 A1* | 12/2015 | Kurisawa | .............. | A61L 31/145 424/497 |

OTHER PUBLICATIONS

Fathi et al (Hydrogels for ocular drug delivery and tissue engineering. BioImpacts, 2015, 5(4), 159-164).*
Rodell et al (Shear-Thinning Supramolecular Hydrogels with Secondary Autonomous Covalent Crosslinking to Modulate Viscoelastic Properties In Vivo. Adv Funct Mater. Jan. 28, 2015; 25(4): 636-644) (Year: 2015).*
Wang et al (Supramolecular polymer assembly in aqueous solution arising from cyclodextrin host—guest complexation. Beilstein J Org Chem. 2016; 12: 50-72) (Year: 2016).*
Kurisawa et al (Injectable biodegradable hydrogels composed of hyaluronic acid-tyramine conjugates for drug delivery and tissue engineering. Chem Commun (Camb). Sep. 14, 2005;(34):4312-4. Epub Jul. 28, 2005). (Year: 2005).*
Flores et al (Inclusion Complexation of Phenol Derivatives with a β-Cyclodextrin Based Polymer. J Incl Phenom Macrocycl Chem 53, 63-68 (2005)) (Year: 2005).*
Tran et al (Supramolecular Hydrogels Exhibiting Fast in Situ Gel Forming and Adjustable Degradation Properties. Biomacromolecules 2010, 11, 617-625) (Year: 2010).*

* cited by examiner

*Primary Examiner* — Jake M Vu
(74) *Attorney, Agent, or Firm* — Vorys, Sater, Seymour & Pease LLP; Mih Suhn Koh

(57) ABSTRACT

Provided are an injectable tissue adhesive hydrogel including gamma-cyclodextrin (γ-CD). When such an injectable tissue adhesive hydrogel including the γ-CD is used as a skin glue, based on a fact that the γ-CD has a bigger hydrophobic cavity than that of α- and β-CDs, the injectable tissue adhesive hydrogel including the γ-CD has stronger interactions than host-guest interactions. In addition, hydrogen bonding in the injectable tissue adhesive hydrogel including the γ-CD can improve both cohesiveness and adhesiveness of gelatin. The injectable tissue adhesive hydrogel including the γ-CD having excellent cell viability is used for adhesion of a skin incision, to thereby effectively promote tissue regeneration.

14 Claims, 13 Drawing Sheets

INJECTABLE TISSUE ADHESIVE HYDROGEL INCLUDING GAMMA-CYCLODEXTRIN AND BIOMEDICAL USE THEREOF

CROSS-REFERENCE TO RELATED APPLICATION

This application claims the benefit of Korean Patent Application No. 10-2016-0040153, filed on Apr. 1, 2016, in the Korean Intellectual Property Office, the disclosure of which is incorporated herein in its entirety by reference.

BACKGROUND

1. Field

The present invention relates to an injectable tissue adhesive hydrogel including gamma-cyclodextrin having short curing times and strong tissue adhesiveness, and biomedical uses of the injectable tissue adhesive hydrogel.

2. Description of the Related Art

Supramolecular chemistry is the chemistry based on physical intermolecular interactions (e.g., hydrogen bonding, host-guest interactions, metal coordination, van der Waals forces, and aromatic stacking), and is used in various biomaterial research fields based on a number of advantages. A supramolecular structure can be easily synthesized or prepared by non-covalent bonds that do not require complicated processing steps. In addition, since a supramolecular compound includes non-covalent bonds, it has a reversible property by external physical/chemical stimulation applied thereto. Therefore, such a supramolecular compound can be easily recovered after use, and has advantage as a self-healing compound against external mechanical damage.

Among various supramolecular compounds, cyclodextrins (CDs) have received much attention for biological applications thereof. The CDs are torus-shaped cyclic oligomers consisting of 6, 7, and 8 glucopyranos units, wherein each of the glucopyranos units is connected via an α-(1-4)-glycosidic bond, and are respectively named as alpha-CD (α-CD), beta-CD (β-CD), and gamma-CD (γ-CD).

The CDs each consist of an outer portion with a hydrophilic surface and a hydrophobic inner portion. The hydrophilic surface of the outer portion has hydrogen bonds that facilitate interactions with surrounding molecules, and the hydrophobic inner portion facilitates physical binding with various hydrophobic guests. Here, the hydrophobic inner portion may lead to formation of a physical assembly by host-guest interactions in an aqueous condition and even in a solid-state condition.

In the pharmacy field, the CDs may improve drug solubility and control drug release behavior by forming a host-guest composite with a hydrophobic drug, thereby improving drug bioavailability. In the biomedical field, micelles, layer-by-layer hollow microcapsules, or polymer hydrogels have been prepared in various shapes through assembly or aggregation of cyclodextrin-based polymers at the nanoscale level.

Use of a hydrogel-based tissue glue may save time, as compared to the time required for a suturing process, and requires no high-level technique. In addition, based on advantages such as less traumatic sutures, less pain, no need to remove a suture thread, and local release of a drug, the hydrogel-based tissue glue is known as an excellent material in a variety of clinical applications including hemostasis, wound closure and healing, and the like. When applied to friable tissues such as the dura mater, lung, liver, spleen, and kidney, the hydrogel-based tissue glue plays a particularly important role.

However, regardless of such advantages, the hydrogel-based tissue glue does not satisfy clinical requirements such as strong and rapid adhesiveness, low immunogenicity, and biodegradability, and thus, the application of the hydrogel-based tissue glue as a tissue adhesive has been still limited. In order to overcome such limitations, there is a great need to develop an injectable tissue adhesive hydrogel including a CD, the injectable tissue adhesive hydrogel being excellent in biocompatibility and having excellent mechanical strength through a cross-linking reaction and strong adhesiveness through fast gelation.

However, considering that an injectable tissue adhesive hydrogel including α-CD has relatively low adhesiveness due to the presence of a small hydrophobic cavity and that an injectable tissue adhesive hydrogel including β-CD has relatively low adhesiveness due to the low solubility, it is necessary to research and develop an injectable tissue adhesive hydrogel including γ-CD, which can improve the adhesiveness and has excellent skin regeneration promoting ability.

PRIOR ART DOCUMENT

Patent Document

KR 2014-0091259

SUMMARY

One or more embodiments include an injectable tissue adhesive hydrogel including γ-cyclodextrin (γ-CD), wherein the injectable tissue adhesive hydrogen includes γ-CD having short curing times and strong adhesiveness, and is used for adhesion of a skin incision, to thereby effectively promote tissue regeneration.

Additional aspects will be set forth in part in the description which follows and, in part, will be apparent from the description, or may be learned by practice of the presented embodiments.

According to one or more embodiments, there is provided an injectable tissue adhesive hydrogel including γ-CD, wherein the injectable tissue adhesive hydrogel is cross-linked in situ by adding horseradish peroxidase and hydrogen peroxide to a mixture including at least one γ-CD, which is substituted or unsubstituted with a thiol group, and at least one homogeneous or heterogeneous polymer with a main chain in which phenol or a derivative thereof and at least one functional group selected from an amino group and a carboxyl group are contained.

According to one or more embodiments, there is provided a substance for tissue adhesion and hemostasis, including the injectable tissue adhesive hydrogel.

According to one or more embodiments, there is provided an implant substance for tissue regeneration and augmentation, including the injectable tissue adhesive hydrogel.

According to one or more embodiments, there is provided a carrier for delivering a biologically active substance or drug, including the injectable tissue adhesive hydrogel.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
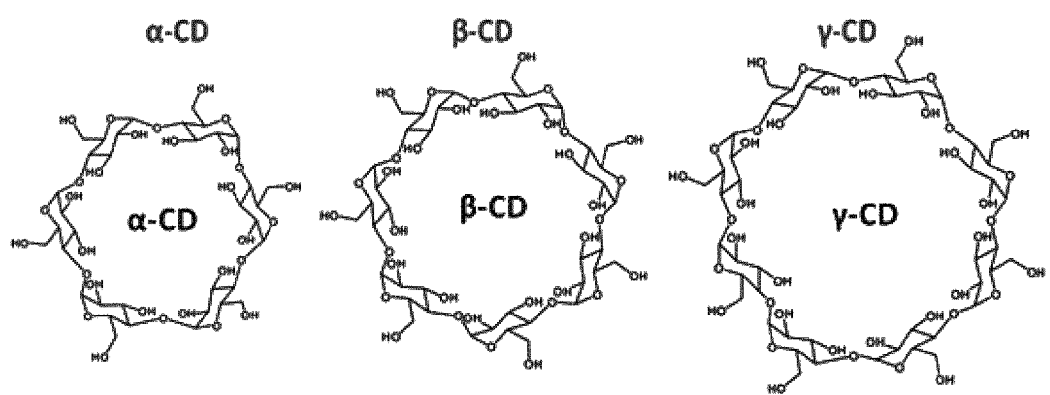
FIG. 1 is a diagram showing a structure of each of α-cyclodextrin, β-cyclodextrin, γ-cyclodextrin.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

The present inventive concept has been completed by figuring out the following factors: gamma-cyclodextrin (γ-CD) including a bigger hydrophobic cavity than alpha-cyclodextrin (α-CD) may include two guests, concomitantly leading to stronger host-guest interactions; due to high affinity of gelatin/γ-CD with tissues, the gelatin/γ-CD may exhibit higher adhesiveness than that of gelatin/α-CD; and due to excellent solubility of the gelatin/γ-CD in comparison with beta-cyclodextrin (β-CD), the gelatin/γ-CD may exhibit more improved adhesiveness that that of an injectable tissue adhesive hydrogel including β-CD.

The present inventive concept provides an injectable tissue adhesive hydrogel, wherein the injectable tissue adhesive hydrogel is cross-linked in situ by adding horseradish peroxidase and hydrogen peroxide to a mixture including at least one γ-CD, which is substituted or unsubstituted with a thiol group, and at least one homogeneous or heterogeneous polymer with a main chain in which phenol or a derivative thereof and at least one functional group selected from an amino group and a carboxyl group are contained.

Figure 3:
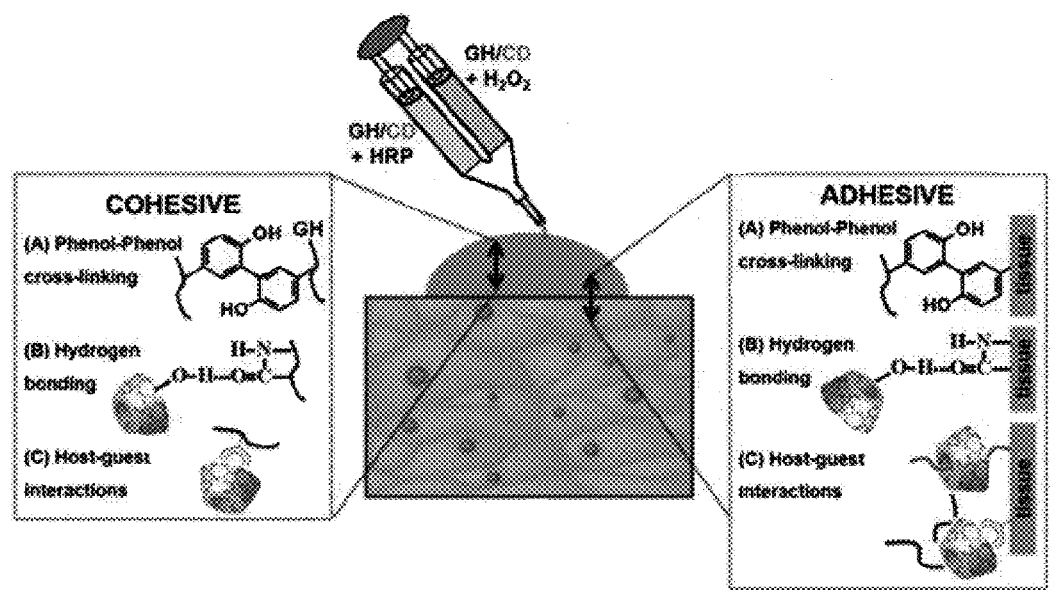
FIG. 3 is a diagram showing details regarding cohesiveness and adhesiveness of a gelatin-tyramine/γ-cyclodextrin glue.

Referring to FIG. 3, the hydrogel forms its basic hydrogel through bonding between phenols or derivatives thereof contained in a side branch of the main chain of the polymer. In addition, hydrogen bonding between γ-CD having 18 to 24 hydroxyl groups and at least one functional group selected from an amino group and a carboxyl group contained in the main chain of the polymer, and host-guest interactions between the polymer and the γ-CD lead to formation of additional bonding in the hydrogel, thereby forming the hydrogel with improved mechanical strength.

In addition, the hydrogel may improve tissue adhesiveness by host-guest interactions between the γ-CD and phenol-derivates in tissues, and by hydrogen bonding between the γ-CD and tissues having a polar group, but embodiments are not limited thereto.

Figure 2:
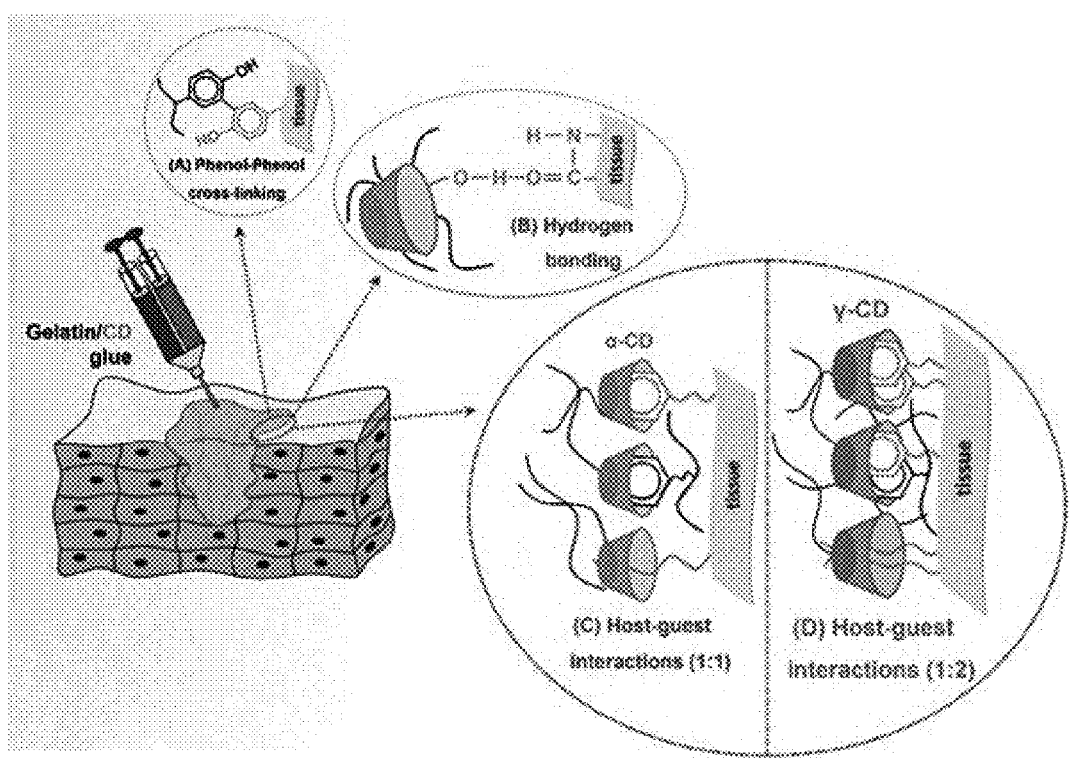
FIG. 2 is a diagram showing phenol-phenol cross-linking (A), hydrogen bonding (B), and host-guest interactions at a ratio of 1:1 (C) and a ratio of 1:2 (D), between a tissue adhesive hydrogel including cyclodextrin and a biological tissue.

Referring to FIGS. 1 and 2, the γ-CD is found to have a bigger hydrophobic cavity than hydrophobic cavities of the α-CD and the β-CD. Accordingly, the γ-CD has host-guest interaction at a ratio of 1:2, whereas the α-CD and the β-CD each have host-guest interaction at a ratio of 1:1. In this regard, in comparison with an injectable tissue adhesive hydrogel including the α-CD and/or the β-CD, an injectable tissue adhesive hydrogel including the γ-CD is found to have excellent cohesiveness and adhesiveness.

In an embodiment, the main chain of the polymer may include at least one selected from the group consisting of gelatin, chitosan, heparin, cellulose, dextran, dextran sulfate, chondroitin sulfate, keratin sulfate, dermatan sulfate, alginate, collagen, albumin, fibronectin, laminin, elastin, vitronectin, hyaluronic acid, fibrinogen, and a multi-arm polymer, but embodiments are not limited thereto.

In an embodiment, the multi-arm polymer may include at least one selected from the group consisting of at least one multi-arm polyethylene glycol (PEG), such as 3-arm-PEG, 4-arm-PEG, 6-arm-PEG, or 8-arm-PEG; and 4-arm-PPO-PEO (Tetronic series), but embodiments are not limited thereto.

In an embodiment, a physiochemical property of the hydrogel, such as gelation time, degradation time, mechanical strength, and water content, may be adjusted by controlling a concentration of the horseradish peroxidase and the hydrogen peroxide.

In an embodiment, the hydrogel may be cross-linked in situ with the aid of a dual syringe kit, but embodiments are not limited thereto.

In an embodiment, the dual syringe kit may be mounted with a spraying nozzle through which the hydrogel is sprayed, but embodiments are not limited thereto.

In an embodiment, the hydrogel may be formed into a sheet or a disc using the dual syringe kit in combination with a Teflon mold, but embodiments are not limited thereto.

In addition, the present inventive concept provides a substance for tissue adhesion and hemostasis, including the injectable tissue adhesive hydrogel described above.

In an embodiment, the substance for hemostasis may be applicable to a medical case selected from the group consisting of cerebral nervous surgery including vascular surgery, orthopedic surgery including bone bonding, hemostasis in patient with a laceration, closure of the femoral artery, closure after incision of an eye affected with a cataract, healing of cartilage and articular cartilage, dermal adhesion, hemostasis at incised portions in organs/secretory glands, anastomosis of gastrointestinal organs, and healing of ligaments and tendons, but embodiments are not limited thereto.

In addition, the present inventive concept provides an implant substance for tissue regeneration and augmentation, including the injectable tissue adhesive hydrogel described above.

In an embodiment, the implant substance may be applicable to one selected from the group consisting of cartilage regeneration, bone regeneration, periodontal regeneration, skin regeneration, cardiac tissue regeneration, artificial intraocular lens, spinal cord regeneration, cranial regeneration, vocal regeneration and augmentation, adhesiveness barrier, urinary incontinence treatment, wrinkles removal augmentation, wound dressing, tissue augmentation, and intervertebral disc treatment, but embodiments are not limited thereto.

In addition, the present inventive concept provides a carrier for delivering a biologically active substance or drug, including the injectable tissue adhesive hydrogel described above.

In an embodiment, the biologically active substance or drug may be selected from the group consisting of a peptide or protein drug, an antibacterial agent, an anti-cancer agent, and an anti-inflammatory agent, and a combination thereof, but embodiments are not limited thereto.

In an embodiment, the peptide or protein drugs may include one selected from the group consisting of fibroblast growth factor (FGF), vascular endothelial growth factor (VEGF), transforming growth factor (TGF), bone morphogenetic protein (BMP), human growth hormone (hGH), porcine growth hormone (pGH), granulocyte-colony stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-$\alpha,\beta,\gamma$, interleukin-2 (IL-2), calcitonin, nerve growth factor (NGF), growth hormone releasing hormone, angiotensin, luteinizing hormone releasing hormone (LHRH), luteinizing hormone releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, vaccines, and a combination thereof, but embodiments are not limited thereto.

In an embodiment, the antibacterial agents may include one selected from the group consisting of minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, fusidic acid and a combination thereof, but embodiments are not limited thereto.

In an embodiment, the anti-cancer agents may include one selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D and a combination thereof, but embodiments are not limited thereto.

In an embodiment, the anti-inflammatory agents may include one selected from the group consisting of acetaminophen, aspirin, ibuprofen, diclofenac, indometacin, piroxicam, fenoprofen, flubiprofen, ketoprofen, naproxen, suprofen, loxoprofen, cinnoxicam, tenoxicam, and a combination thereof, but embodiments are not limited thereto.

Hereinafter, the present invention will be described more fully with reference to the following examples. However, these examples are for illustrative purposes only, and thus, should not be construed as being limited to the examples set forth herein.

<Example 1> Preparation of Materials

Gelatin (type A from porcine skin, >300 bloom), 3-(4-hydroxyphenyl)propionic acid (HPA), 1-ethyl-3-(3-dimethylaminopropyl)-carbodiimide (EDC), N-hydroxysuccinimide (NHS), peroxidase from horseradish (HRP, type VI, 250-330 units/mg solid), hydrogen peroxide ($H_2O_2$), and collagenase type II were purchased from Sigma Aldrich (St. Louis, Mo., USA), and dimethylformamide (DMF) was purchased from Junsei (Tokyo, Japan).

$\alpha$-CD ($M_w$=972.85 g/mol), $\beta$-CD ($M_w$=1134.98 g/mol), and $\gamma$-CD ($M_w$=1297.12 g/mol) were purchased from Tokyo Chemical Industry Co., Ltd (T.C.I, Tokyo, Japan).

Fibrin gel with two components (Tissucol Duo 500) was purchased from Baxter AG (Volkitswil, Switzerland).

Dulbecco's Modified Eagle's Medium (DMEM), penicillin-streptomycin (P/S), and trypsin/EDTA were purchased from Gibco BRL (Grand Island, N.Y., USA), and getal bovine serum (FBS) and Dulbecco's phosphate buffered saline (DPBS) were purchased from Wisent (Saint-Bruno, QC, Canada). In addition, Live/Dead Viability/Cytotoxicity Assay Kit was purchased from Invitrogen (USA), and EZ-Cytox enhanced cell viability assay kit (WST-1 assay reagent) was purchased from ITSBIO (Seoul, South Korea). Other chemicals and solvents were used without further purification.

<Example 2> Synthesis of 3-(4-hydroxyphenyl)propionic Acid-Conjugated Gelatin (GH) Polymer A GH polymer was synthesized by coupling 3-(4-hydroxylphenyl)propionic acid (HPA) with gelatin in the presence of EDC and NHS according to the method known in the art.

3.83 g (20 mmol) of EDC dissolved in 15 mL of co-solvent of $H_2O$ was mixed with DMF at a ratio of 3:2, and then, the mixed solution was added into a solution in which 3.32 (20 mmol) of HPA was dissolved in 125 mL of co-solvent.

After 1 hour of activation, a co-solvent solution in which 3.45 g (30 mmol) of NHS dissolved in 15 mL of $H_2O$ was mixed with DMF at a ratio of 3:2 was added to the activated reaction solution with stirring for 1 hour.

The activated HPA solution was then poured into a gelatin solution (5 g in 150 mL DI water, 40° C.).

The reaction between the activated HPA solution and the gelatin solution was allowed for 24 hours, and the temperature was maintained to 40° C. so that gelatin was able to be dissolved in the HPA solution homogeneously.

The reacted mixture was subjected to ultrafiltration using a dialysis tube having 3,500 kDa MWCO at a temperature of 40° C., and the media was changed 3 times per day for 3 days. After freeze-drying, the GH polymer was obtained with yield of 78.8%.

<Example 3> Modification of Gold Surface

A gold substrate (8×10 $mm^2$) was fabricated by a resistive evaporation process using gold onto a Ti-primed Si wafer.

A surface of the gold substrate was immersed in piranha solution ($H_2SO_4$:$H_2O_2$=4:1) for 15 minutes. The immersed surface of the gold substrate was washed with deionized water two times, and with ethanol once to remove excessive piranha reagents. The washed gold substrate was dipped into 10 mM of mercaptoethanol and 1 mM of mercaptoundecanoic acid in ethanol for 12 hours. The gold substrate having the modified surface was washed with ethanol three times, and then, named as a Au-C11 substrate.

After the Au-C11 substrate was immersed in aqueous 1 mM EDC solution for 15 minutes, an aqueous 1 mM NHS solution was added thereto, and then, cultured for 15 minutes to synthesize the mixture. A solution containing 1 mM of 4-amino phenol in DMSO was supplemented into the mixture, and a reaction was allowed for 1 hour. The modified substrate formed by the two steps above was named as a Au-C11-Phenol substrate, which was washed again with ethanol three times.

<Experimental Example 1> Hydrogel Formation and Gelation Time

The GH polymer (10 wt %) was dissolved at a temperature of 40° C. To fabricate a GH/CD hydrogel immersed with α, β, γ-CDs, an α-CD solution, a β-CD solution, and a γ-CD solution, each having a concentration of 10 wt %, were prepared. 10 wt % GG was added to the CD solutions, to thereby have the ratio 1/1 w/w and prepare mixtures, such as GH/α-CD 5/5 wt % (GH5/α-CD5), GH/β-CD 5/5 wt % (GH5/β-CD5), and GH/γ-CD 5/5 wt % (GH5/γ-CD5). Detailed preparation conditions for tissue adhesive hydrogels are shown in table 1.

TABLE 1

| Hydrogel | Composition |
|---|---|
| GH5 | GH 5 wt % + $H_2O$ 95 wt % |
| GH5/α-CD5 | GH 5 wt % + α-CD 5 wt % + $H_2O$ 90 wt % |
| GH5/β-CD5 | GH 5 wt % + β-CD 5 wt % + $H_2O$ 90 wt % |
| GH5/γ-CD5 | GH 5 wt % + γ-CD 5 wt % + $H_2O$ 90 wt % |

All mixtures were heated up to 40° C. for 30 minutes, and then, vortexed to ensure complete melting of gelatin and system homogenization.

During the experiment process, the temperature of the polymer solution was maintained to a temperature of about 40° C. to prevent the physical gelling formation of gelatin at a low temperature (equal to or less than 23° C.). Here, the gelation time for a gelatin glue and a gelatin/CD glue was determined by a vial tilting method.

90 μl of a polymer solution and 10 μl of an HRP solution were added to a microtube (solution A) while 90 μl of the polymer solution and 10 μl of $H_2O_2$ were added to another microtube (solution B). Solutions A and B were mixed and smoothly vortexed to form hydrogels. The mixed solution was smoothly shaken at room temperature until no flow was observed.

To examine the gelation time of the gelatin glue and the gelatin/CD glue as a function of the HRP concentration, the HRP concentration was varied in a range from about 0.003 mg/mL to about 0.01 mg/mL. All samples were tested in triplicate for each experiment condition.

As a result of the experiment, the gelation time for the hydrogels was able to be adjusted in a range from about 10 seconds to about 210 seconds by controlling the HRP concentration. Accordingly, it was confirmed that the increase in the HRP concentration has shortened the hydrogel formation time. That is, the increase in the HRP concentration stimulated the decomposition of $H_2O_2$, and accordingly, the rate of formation of radicals was accelerated as well. Since the gels were formed by the generated radicals, the hydrogel formation time was shortened.

In addition, as the CDs were used for immersion, the gelation time was relatively increased, as compared to GH5 which is a control. In this regard, it was confirmed that, at the time of cross-linking of the CDs, the phenol-derivates contained the polymer or the interactions between amine groups and carboxyl groups contained in the main chain of the polymer have affected the gel formation.

Figure 4:
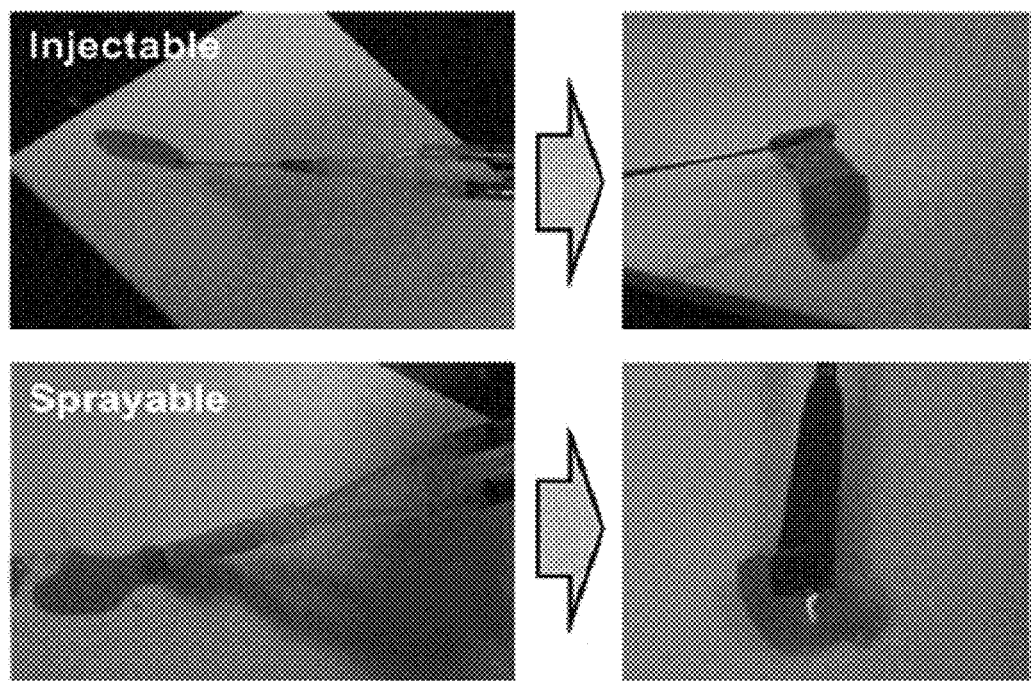
FIG. 4 is a diagram schematically describing preparation of a hydrogel according to Experimental Example 1.

FIG. 4 is a diagram schematically describing preparation of an injectable and sprayable hydrogel using a dual syringe kit.

Figure 5:
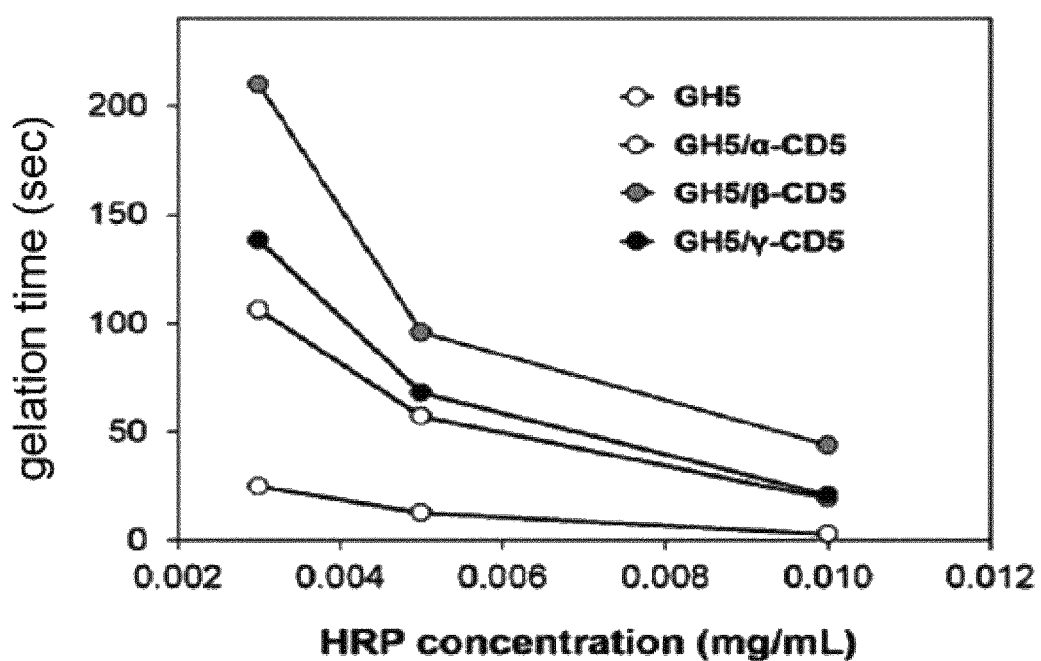
FIG. 5 is a graph showing gelation time of a hydrogel according to Experimental Example 1.

FIG. 5 is a graph showing results of the comparison evaluation on the gelation time for the GH5 hydrogel as a control and the GH5/α-CD5, GH5/β-CD5, and GH5/γ-CD5 hydrogels according to the HRP concentrations.

<Experimental Example 2> Evaluation of Elastic Modulus

Under conditions of 0.03% $H_2O_2$ and 0.005 mg/mL HRP, hydrogels having compositions of GH, GH/α-CD, GH/β-CD, and GH/γ-CD were prepared in the same manner as described above in connection with the gelation time. Then, a rheometer was used to measure elastic modulus of the prepared hydrogels. Here, the experiment conditions included a plate having a diameter of 25 mm, a temperature of 37° C., and a measurement for 10 minutes.

The GH5 hydrogel which is a control showed elastic modulus of 12,200 Pa. When the CDs having a concentration of 5 wt % were additionally added, the resulting hydrogel showed relatively increased elastic modulus than that of the GH5 hydrogel. As a result of the experiment, the hydrogels having the compositions of GH5/α-CD5, GH5/β-CD5, and GH5/γ-CD5 each showed elastic modulus of 15,800 Pa, 13,100 Pa, and 17,580 Pa. That is, it was confirmed that the CDs immersed with the hydrogel induced hydrogen bonding within the GH polymer network and the host-guest interactions, so that the hydrogel was further cross-linked.

In particular, the γ-CD having excellent solubility and host-guest interactions compared to the α-CD and the β-CD exhibited the highest elastic modulus under the same wt % conditions (5 wt %).

Figure 6:
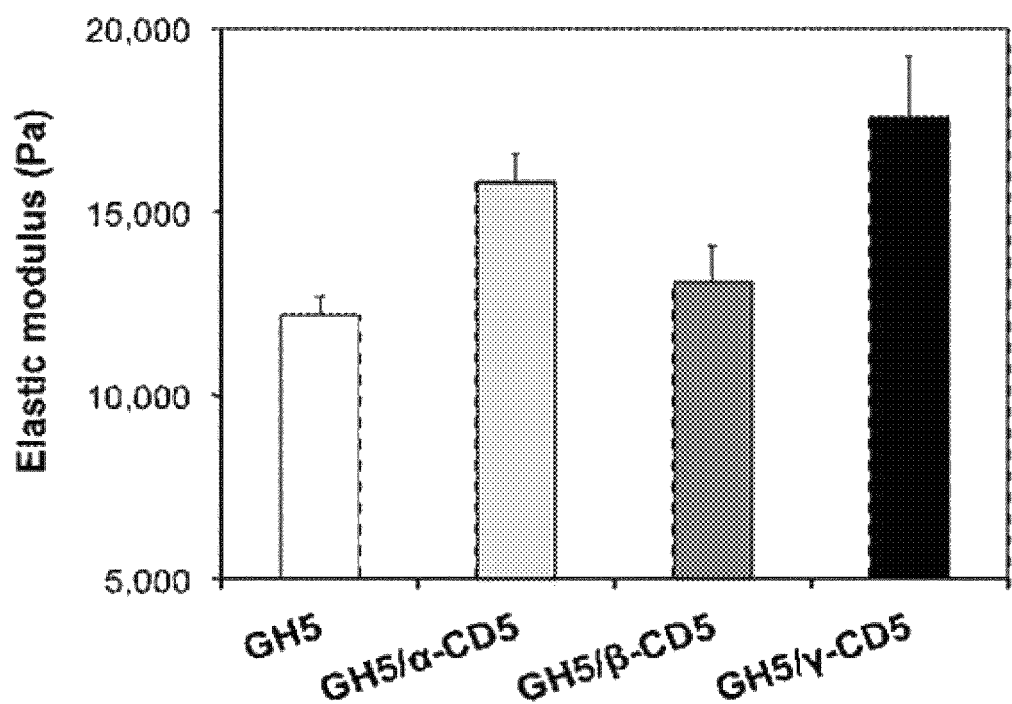
FIG. 6 is a graph showing mechanical strength of a hydrogel, such as elastic modulus, according to Experimental Example 2.

FIG. 6 is a graph showing elastic modulus results of the GH5 hydrogel and the hydrogels having the compositions of GH5/α-CD5, GH5/β-CD5, and GH5/γ-CD5.

<Experimental Example 3> Evaluation of Adhesiveness

According to the evaluation method of ASTM F2255-03 ("Test Method for Strength Properties of Tissue Adhesives in Lap-Shear by Tension Loading"), the tissue adhesive strength of the hydrogel on porcine skin was measured using a hydraulic universal testing machine (UTM). Here, as a control, a fibrin glue and a GH hydrogel in which the CD was not immersed were used.

The dimension of the porcine skin was about 2.5 cm, and every piece of the porcine skin was attached on a rectangle plastic substrate using an ethyl cyanoacrylate glue.

Before testing, isopropanol 70% was used in deionized water to clean the skin surface for decellularization. After 15 minutes, 100 μl of the glue was applied to cover an area of porcine skin, and then two surfaces were lapped together. The adhesive joint was kept at room temperature for 60 minutes in a humid environment under the force of 100 g.

The samples were then loaded to failure in shear with a crosshead speed of 10 mm/min. The maximum strength versus displacement was measured, and the shear stress at break (ultimate adhesion strength) was used to characterize adhesion for each sample. At least five samples were used for each measurement.

When evaluating adhesiveness of the gelatin/CD glue using the gold substrate, the modified gold substrate (8×10 mm) was used in the same manner as described above in connection with the measurement of the porcine skin.

Figure 7:
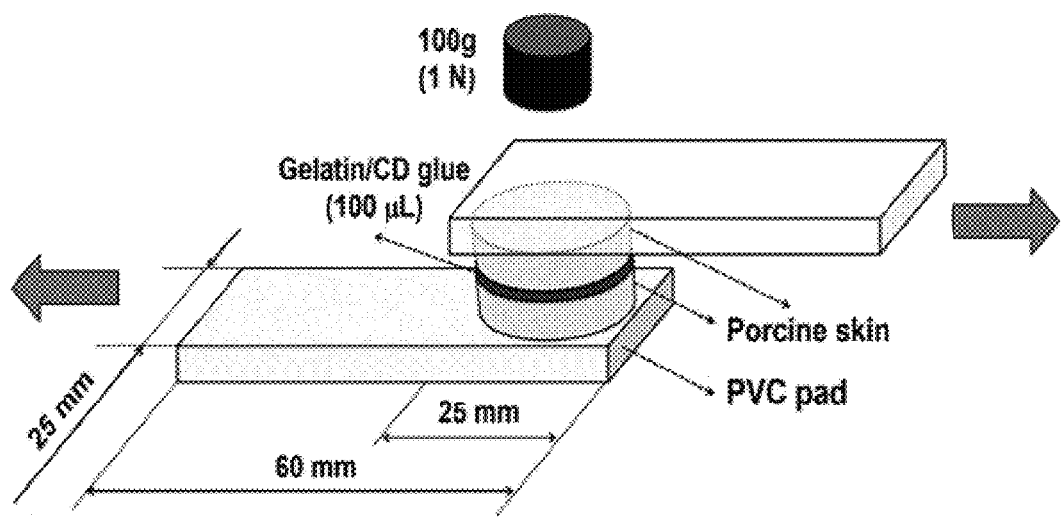
FIG. 7 is a diagram describing an embodiment of a method of evaluating adhesiveness of a hydrogel according to Experimental Example 3.
Figure 8:
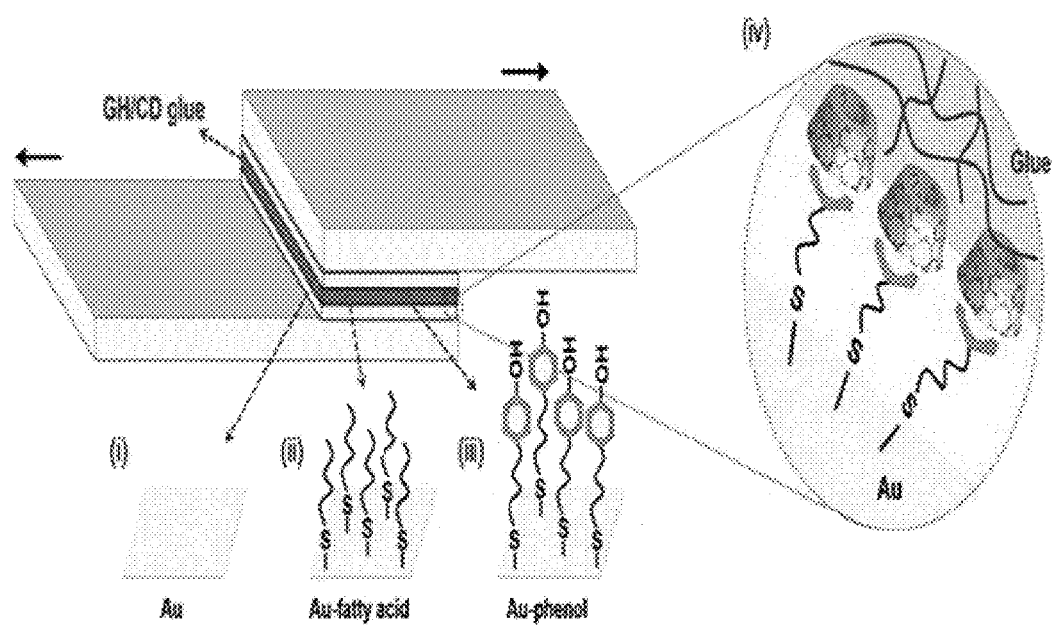
FIG. 8 is a diagram describing another embodiment of a method of evaluating adhesiveness of a hydrogel according to Experimental Example 3.

FIGS. 7 and 8 are each a diagram describing a method of testing adhesiveness of the hydrogel using the porcine skin and the gold substrate according to embodiments.

As a result of evaluating the tissue adhesive strength was evaluated by using the porcine skin, it was confirmed that the increased concentration of the CD being immersed led to the improved tissue adhesive strength. In particular, in comparison with the α-CD and the β-CD, the γ-CD showed the strongest tissue adhesive strength. In this regard, it was confirmed that such strong tissue adhesive strength was influenced by improved cohesiveness and adhesiveness of the hydrogel. Regarding the β-CD having limited solubility, the inclusion of the β-CD at a concentration of 5 wt % rather showed reduced tissue adhesive strength.

Regarding GH/γ-CD showing the strongest tissue adhesive strength among the CDs, as the wt % of the polymer and the concentration of the γ-CD being immersed increased, the hydrogel showed tissue adhesive strength in a range of about 24,250 Pa to about 95,020 Pa. The hydrogel showed the tissue adhesive strength that was 20 times higher than that of the fibrin glue which is a control (4,560 Pa).

In addition, to understand the interactions between tissues and the tissue adhesive hydrogel, the tissue adhesive strength of the hydrogel was evaluated using the gold substrate to which a phenol group was introduced. Consequently, the results of the evaluation were similar with those obtained by evaluating the tissue adhesive strength using the porcine skin. The GH/γ-CD hydrogel showed relatively improved adhesiveness compared to the GH/α-CD hydrogel, and such improvement was explained by that, under the same wt % conditions (5 wt %), the γ-CD had strong host-guest interactions and included derived phenol molecules on the gold substrate, as compared to the α-CD.

Figure 9A:
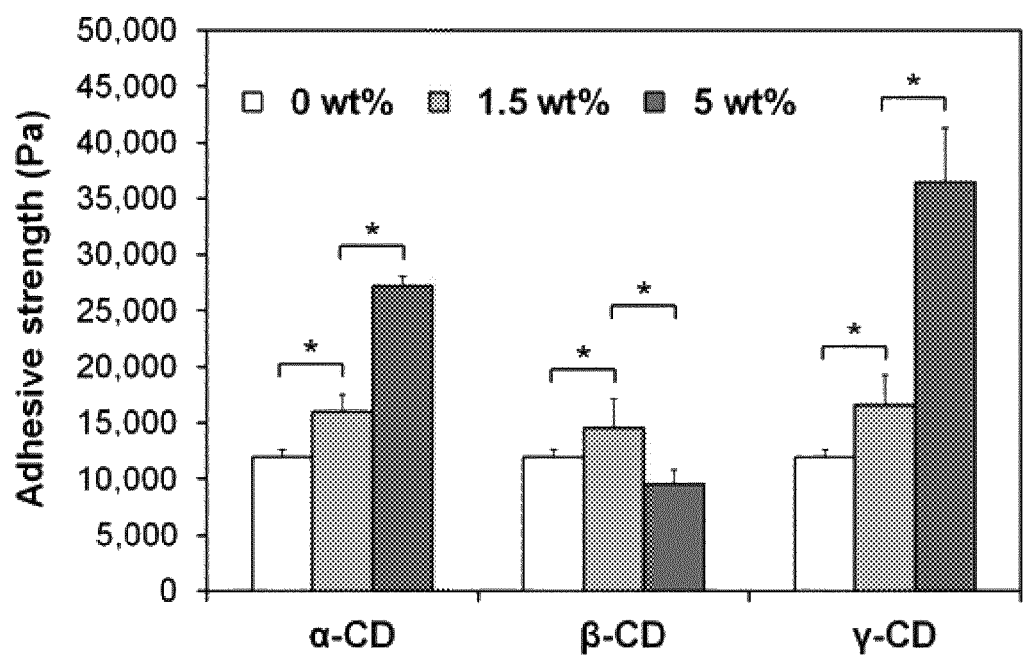
FIGS. 9A and 9B are each a graph showing results of tissue adhesive strength of a hydrogel under tissue conditions according to Experimental Example 3.
Figure 9B:
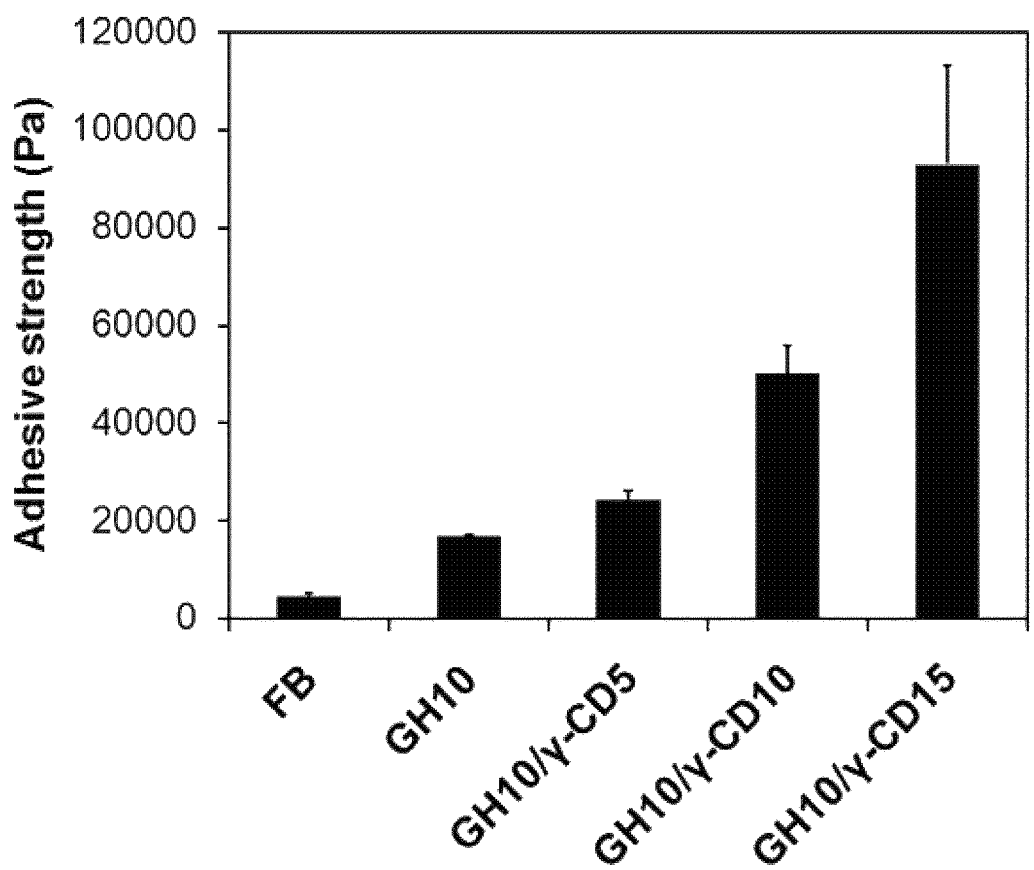

FIG. 9A is a graph showing tissue adhesive strength of the hydrogel on the porcine skin according to the concentration of the CDs in each of the GH5 hydrogel, which is a control, and the hydrogels having the compositions of GH5/α-CD, GH5/β-CD, and GH5/γ-CD, and FIG. 9B is a graph showing tissue adhesive strength of the hydrogel on the porcine skin according to the concentration of the γ-CD in each of the fibrin glue, which is a control, and the hydrogel having the composition of GH10.

Figure 10:
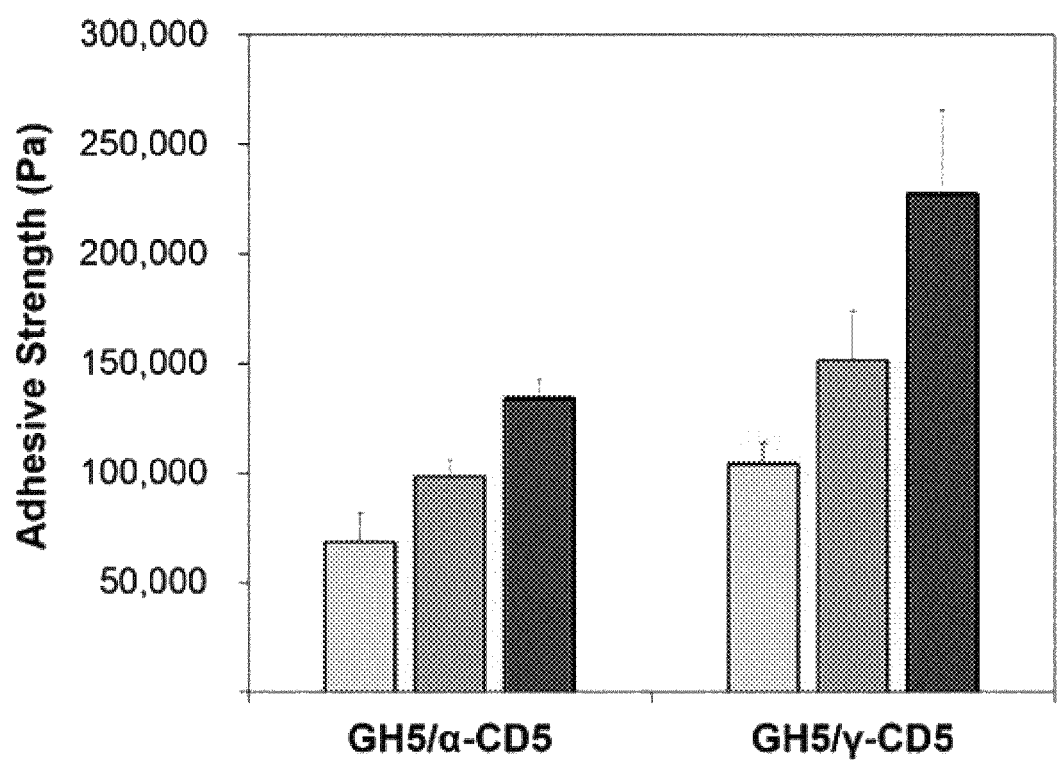
FIG. 10 is a graph showing results of tissue adhesive strength of a hydrogel under gold substrate conditions according to Experimental Example 3.

FIG. 10 is a graph showing tissue adhesive strength of the hydrogel on the gold substrate according to the concentration of the CDs in each of the hydrogels having the compositions of GH5/α-CD and GH5/γ-CD.

<Experimental Example 4> Evaluation of Biodegradation

To determine biodegradation of the gelatin glue, 300 µl of a hydrogel glue was fabricated in a microtube in the same manner as in the gelation time test.

To evaluation the effect of the CDs on a degradation rate of the gelatin glue, GH5, GH5/α-CD2.5 and GH5/α-CD5 glues were formed with $H_2O_2$ concentration of 0.3% and HRP concentration of 0.005 mg/mL.

After 30 minutes for stabilization of the hydrogel samples at room temperature, the weight of each of the glue sample was recorded. Afterwards, an enzymatic treatment using collagenase (0.005 mg/mL) was performed on the hydrogel samples. At the specific time intervals, the hydrogel samples were weighed after removing the supernatant completely, and then, 1 mL of a fresh media was added. Here, the degree of degradation was calculated using the following equation:

$$\text{Weight of hydrogels } (\%) = \frac{W_d}{W_i} \times 100 \qquad \text{[Equation 1]}$$

Here, $W_d$ and $W_i$ indicate the weights of the degraded and original hydrogels, respectively.

As a result of the experiment, it was confirmed that all hydrogel samples were time-dependently degraded upon the enzymatic treatment using collagenase at a concentration of 0.005 mg/mL. Here, the hydrogel samples in which the CD was immersed showed relatively delayed degradation behavior. In particular, the hydrogel having the composition of GH5/γ-CD5 showed the slowest degradation behavior among the hydrogels having the compositions of GH5/α-CD5 and GH5/β-CD5, and such slow behavior can be explained by the improved elastic modulus (i.e., high cross-linking) of the hydrogel having the composition of GH5/γ-CD5.

Figure 11:
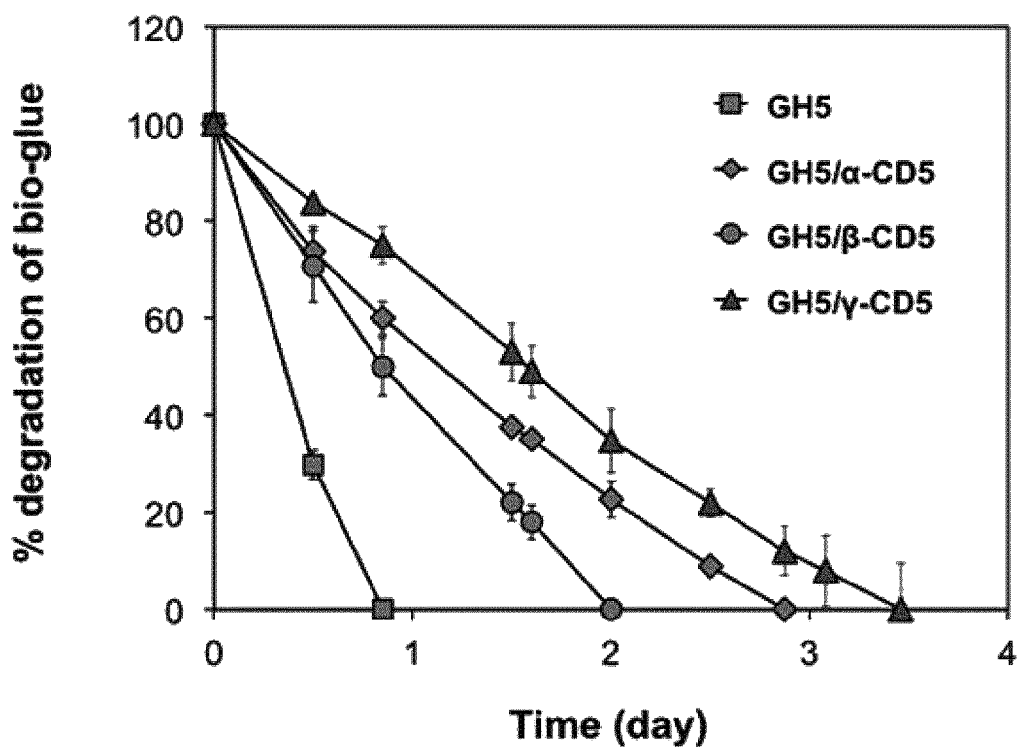
FIG. 11 is a graph showing results of evaluation on biodegradation of a hydrogel according to Experimental Example 4.

FIG. 11 shows the time-dependent degradation behavior of the GH5 hydrogel and the hydrogel having the compositions of GH5/α-CD5, GH5/β-CD5, and GH5/γ-CD5, resulted according to the treatment using collagenase.

<Experimental Example 5> Evaluation of Cytotoxicity of Tissue Adhesive Hydrogel

To evaluate in vitro cytotoxicity, 300 µl of the GH5 hydrogel and the hydrogels having the compositions of GH5/α-CD5, GH5/β-CD5, and GH5/γ-CD5 were each fabricated in a 24-well plate. Then, fibroblasts were cultured on surfaces of the hydrogels to perform the cytotoxicity evaluation. The concentration of the cells used herein was about $1 \times 10^4$ cells/wells, and the culturing of the cells was performed at a temperature of 37° C. under 5% $CO_2$ atmosphere. After 3 days of the culturing, cell viability was asses using a Live/Dead Viability/Cytotoxicity Assay Kit (Invitrogen, USA). According to the Live/Dead assay, cell apoptosis by the cytotoxicity were shown in red while cells that survived against the cytotoxicity were shown in green to evaluate the presence of the cytotoxicity.

As a result of the experiment, it was confirmed that no apoptosized cells were observed in all hydrogel samples fabricated above, meaning that the hydrogel samples had excellent in vitro biocompatibility.

Figure 12:
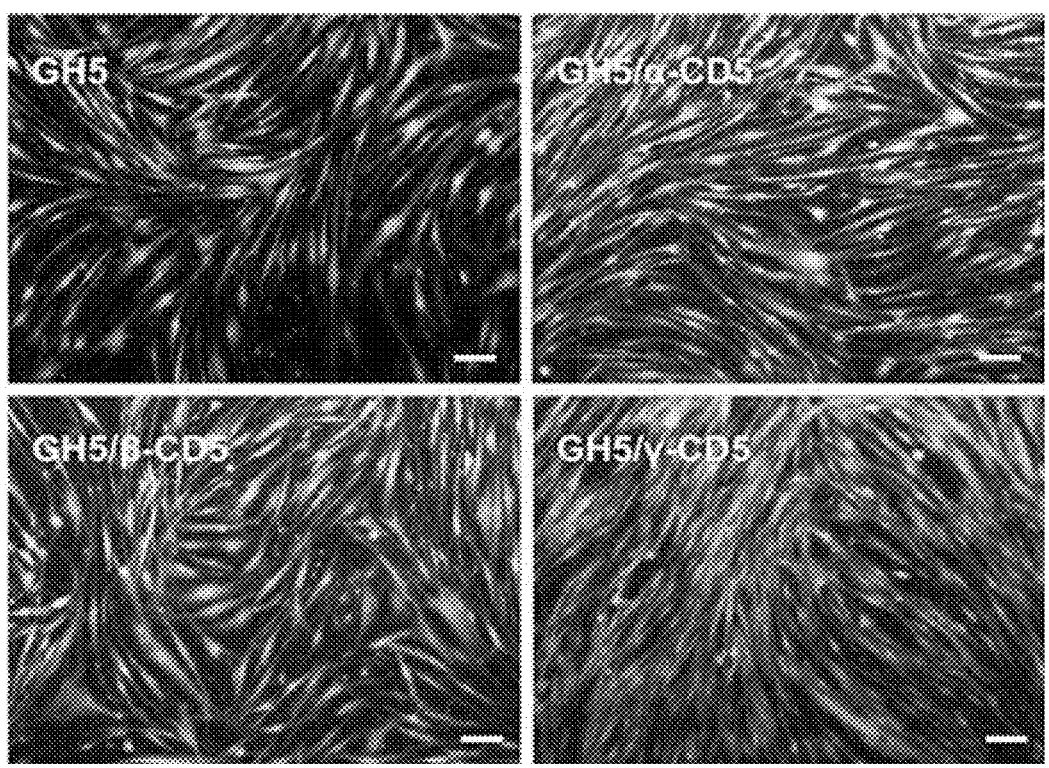
FIG. 12 shows images showing results of cytotoxicity evaluation on a hydrogel according to Experimental Example 5.

FIG. 12 shows images showing results of cytotoxicity evaluation on the GH5 hydrogel and the hydrogels having the compositions of GH5/α-CD5, GH5/β-CD5, and GH5/γ-CD5.

As described above, an injectable tissue adhesive hydrogel including γ-CD having a bigger hydrophobic cavity than hydrophobic cavities of α-CD and β-CD may have strong host-guest interactions. In addition, the injectable tissue adhesive hydrogel can improve both cohesiveness and adhesiveness of gelatin through hydrogen bonding, and furthermore, may be rapidly cured, thereby exhibiting tissue adhesive strength that is at least 20 times higher than that of an existing fibrin glue. In this regard, the injectable tissue adhesive hydrogel disclosed herein can be used as a tissue glue for promoting skin regeneration.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of making an injectable tissue-adhesive hydrogel composition in situ comprising gamma-cyclodextrin (γ-CD),
    wherein the injectable tissue adhesive hydrogel composition is cross-linked in situ by adding horseradish peroxidase and hydrogen peroxide to a mixture comprising at least one γ-CD, which is substituted or unsubstituted with a thiol group, and at least one homogeneous or heterogeneous polymer with a main chain in which phenol or 4-aminophenol and at least one functional group selected from an amino group and a carboxyl group are contained,
    wherein the hydrogel is bonded by host-guest interaction between the at least one homogeneous or heterogeneous polymer and the γ-CD, the hydrogel is cross-linked in situ by phenol-phenol bonding between phenols or 4-aminophenols contained in a side branch of the main chain, and the hydrogel is cross-linked in situ by hydrogen bonding between a hydroxyl group of the γ-CD and the at least one functional group selected from the amino group and the carboxyl group, and
    wherein the homogeneous or heterogeneous polymer is 3-(4-hydroxyphenyl)propionic acid-conjugated gelatin (GH) polymer, and the host-quest interaction between the γ-CD and the polymer is at a ratio of 1:2.

2. The method of claim 1, wherein a physiochemical property of the hydrogel, selected from the group consisting of gelation time, degradation time, mechanical strength, and water content, is adjusted by controlling a concentration of the horseradish peroxidase and the hydrogen peroxide.

3. The method of claim 1, wherein the hydrogel is cross-linked in situ with the aid of a dual syringe kit.

4. The method of claim 3, wherein the dual syringe kit is mounted with a spraying nozzle through which the hydrogel is sprayed.

5. A substance for tissue adhesion and hemostasis, comprising the injectable tissue adhesive hydrogel prepared by the method of claim 1.

6. The substance of claim 5, wherein the substance for hemostasis is applicable to a medical case selected from the group consisting of cerebral nervous surgery including vascular surgery, orthopedic surgery including bone bonding, hemostasis in patient with a laceration, closure of the femoral artery, closure after incision of an eye affected with a cataract, healing of cartilage and articular cartilage, dermal adhesion, hemostasis at incised portions in organs/secretory glands, anastomosis of gastrointestinal organs, and healing of ligaments and tendons.

7. An implant substance for tissue regeneration and augmentation, comprising the injectable tissue adhesive hydrogel prepared by the method of claim 1.

8. The implant substance of claim 7, wherein the implant substance is applicable to one selected from the group consisting of cartilage regeneration, bone regeneration, periodontal regeneration, skin regeneration, cardiac tissue regeneration, artificial intraocular lens, spinal cord regeneration, cranial regeneration, vocal regeneration and augmentation, adhesiveness barrier, urinary incontinence treatment, wrinkles removal augmentation, wound dressing, tissue augmentation, and intervertebral disc treatment.

9. A carrier for delivering a biologically active substance or drug, comprising the injectable tissue adhesive hydrogel prepared by the method of claim 1.

10. The carrier of claim 9, wherein the biologically active substance or drug is selected from the group consisting of a peptide or protein drug, an antibacterial agent, an anti-cancer agent, and an anti-inflammatory agent, and a combination thereof.

11. The carrier of claim 10, wherein the peptide or protein drug comprises one selected from the group consisting of fibroblast growth factor (FGF), vascular endothelial growth factor (VEGF), transforming growth factor (TGF), bone morphogenetic protein (BMP), human growth hormone (hGH), porcine growth hormone (pGH), granulocyte-colony stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-α,β,γ, interleukin-2 (IL-2), calcitonin, nerve growth factor (NGF), growth hormone releasing hormone, angiotensin, luteinizing hormone releasing hormone (LHRH), luteinizing hormone releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, vaccines, and a combination thereof.

12. The carrier of claim 10, wherein the antibacterial agent comprises one selected from the group consisting of minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, am ikacin, tobramycin, dibekacin, cefotaxime, cefaclor, erythromycine, ciprofloxacin, levofloxacin, enoxacin, vancomycin, imipenem, fusidic acid and a combination thereof.

13. The carrier of claim 10, wherein the anti-cancer agent comprises one selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D and a combination thereof.

14. The carrier of claim 10, wherein the anti-inflammatory agent comprises one selected from the group consisting of acetaminophen, aspirin, ibuprofen, diclofenac, indometacin, piroxicam, fenoprofen, flubiprofen, ketoprofen, naproxen, suprofen, loxoprofen, cinnoxicam, tenoxicam, and a combination thereof.

* * * * *